United States Patent
Coates et al.

(10) Patent No.: US 8,672,866 B2
(45) Date of Patent: Mar. 18, 2014

(54) FOOT SUPPORT STRAP

(76) Inventors: Christopher Aaron Coates, Kent, WA (US); Lori Suzanne Coates, Kent, WA (US)

( * ) Notice: Subject to any disclaimer, the term of this patent is extended or adjusted under 35 U.S.C. 154(b) by 0 days.

(21) Appl. No.: 13/589,163

(22) Filed: Aug. 19, 2012

(65) Prior Publication Data
US 2014/0052040 A1    Feb. 20, 2014

(51) Int. Cl.
*A61F 5/00*    (2006.01)
(52) U.S. Cl.
USPC .............................................. 602/23; 602/28
(58) Field of Classification Search
USPC ......... 602/16, 23–28, 60–65; 128/882; 2/455, 2/456
See application file for complete search history.

(56) References Cited

U.S. PATENT DOCUMENTS

| | | | | |
|---|---|---|---|---|
| 3,508,544 A | * | 4/1970 | Moore et al. | 128/892 |
| 4,133,311 A | * | 1/1979 | Karczewski | 602/65 |
| 4,313,433 A | * | 2/1982 | Cramer | 602/27 |
| 5,496,358 A | * | 3/1996 | Rosenwald | 607/108 |
| 6,506,175 B1 | * | 1/2003 | Goldstein | 602/60 |

* cited by examiner

*Primary Examiner* — Michael A. Brown

(57) ABSTRACT

An orthopedic device to provide support, to help heal and prevent plantar fasciitis and alleviate pain caused by plantar fasciitis, heel pain, fallen arches, bunions, neuromas, arthritis and other foot conditions. Said orthopedic device is simple to use, comfortable, non-limiting to daily routines and types of footwear.

4 Claims, 4 Drawing Sheets

FOOT SUPPORT STRAP

BACKGROUND OF THE INVENTION

This application relates to the feet, specifically to offer support, pain relief and a means of healing and preventing plantar fasciitis and various other foot ailments.

A large percentage of the population suffers from foot pain due to overuse, injuries, improper footwear or lack of support to the feet. Many foot ailments such as plantar fasciitis, bunions, fallen arches, neuromas, arch pain and arthritis can develop. These ailments can cause improper bone positioning of the feet, ankles, legs, knees, hips and spine. Because of this misalignment, it can place strain on tendons, muscles and ligaments which can result in debilitating pain. Athletes are most susceptible to foot ailments because of the pounding abuse the feet are subject to during the sport. Many people that must stand on their feet all day have terrible foot pain.

There are many foot braces, tension devices, foot splints, restraint devices, foot wraps, elastic socks and rigid boots on the market that make an attempt the to heal plantar fasciitis by cushioning the foot, holding it in a stretched position or compressing the fascia. However, they do not provide enough relief to the plantar fascia, arches and other parts of the foot to help align the foot itself, relieve the pain and inflammation and allow it to heal. All these devices are very cumbersome and difficult to wear as they do not fit comfortably inside a shoe, nor do they permit daily routine activity. Some of these devices even require the user to become totally inactive in order for the device to work.

There are over-the-counter arch supports as well as custom made arch supports that exist in the market. Finding the right one that fits correctly and comfortably can be very difficult. Switching a pair of arch supports to the many different shoes a person wears can be very inconvenient or very expensive if you have to purchase several pair of arch supports.

Some treatments involve steroid injections, anti-inflammatories, night splints, ice packs and even bed rest and corrective surgery. All these can be very painful, unhealthy and inconvenient.

Even though these devices can provide a small amount of relief, they are typically designed to alleviate just one type of condition. Therefore the need for several different corrective devices is necessary for many different ailments. Purchasing and/or choosing which one to use can be confusing and sometimes can hurt your feet more than help.

Typically, foot and ankle doctors will use athletic tape to tape the foot to alleviate pain and support the foot while healing. While this is a great method, it is extremely inconvenient to have to tape the foot every few days for several weeks as it is difficult and time consuming. The patient cannot afford to go back to their doctor every few days to get their feet re-taped. As a result, the foot gets walked on without being taped and therefore becomes re-injured before it is allowed to heal.

Thus, it is highly desirable to have a system for treating and preventing plantar fasciitis, and the many other foot ailments, that is convenient and comfortable. It is also highly desirable to have a system that can be applied easily by the average person for use for multiple foot ailments that supports the foot, aligns the foot, allows healing as well as using it to wear as an injury prevention device. It is even more desirable to have all of the above in addition to being quick to apply, non-limiting to any activity the user engages in and can be worn with any type of footwear or without footwear at all.

These and other advantages of one or more aspects will become apparent from a consideration of the ensuing description and accompanying drawings.

BRIEF SUMMARY OF THE INVENTION

The foot support strap is a disposable orthopedic device consisting of non-stretch, one-piece, adhesive fabric, providing thin, custom fitting, self-support to the foot for alignment, healing, injury prevention and alleviation of pain from plantar fasciitis, fallen arches, heel pain, bunion pain, arthritis and other foot ailments.

The foot support strap is a flexible fabric, having adhesive applied to one side so that it custom fits comfortably onto a foot of any size and shape. It helps to align the foot, self supports the arch of the foot and takes the tension off the plantar fascia, relieving pain in many areas of the foot. It is very quick and easy to apply and the foot support strap is completely hidden while wearing a normal shoe. It can be worn with any type of shoe on the market or without any shoes at all. There is no need for expensive arch supports, special shoes, foot wraps, splints, boots, special socks, tension and restraint devices or cumbersome foot braces.

Thus, several advantages of one or more aspects are to provide continued support, alignment, alleviate pain, prevent injuries and promote healing of many foot ailments with comfort and convenience.

DETAILED DESCRIPTION

The foot support strap is an adhesive, one-piece, fabric strap that can be quickly applied to any foot to prevent and aide the healing of several foot ailments, such as plantar fasciitis, bunions, fallen arches, neuromas, arch pain and arthritis. The foot support strap is simple to apply, convenient to use in any situation and non-restricting to any type of footwear.

The foot support strap is constructed so that the ball of the foot and heel of the foot are not allowed to stretch apart when the foot steps down. Because the foot is being held together, the foot support strap does not allow the arch to fall nor does it allow the plantar fascia tendon to be stretched. Thus, the foot is being aligned and supported. Therefore, the tears and inflammation in a foot ailment, such as plantar fasciitis and other foot ailment areas, are allowed to heal while the foot support strap is being worn on the foot.

Figure 1:
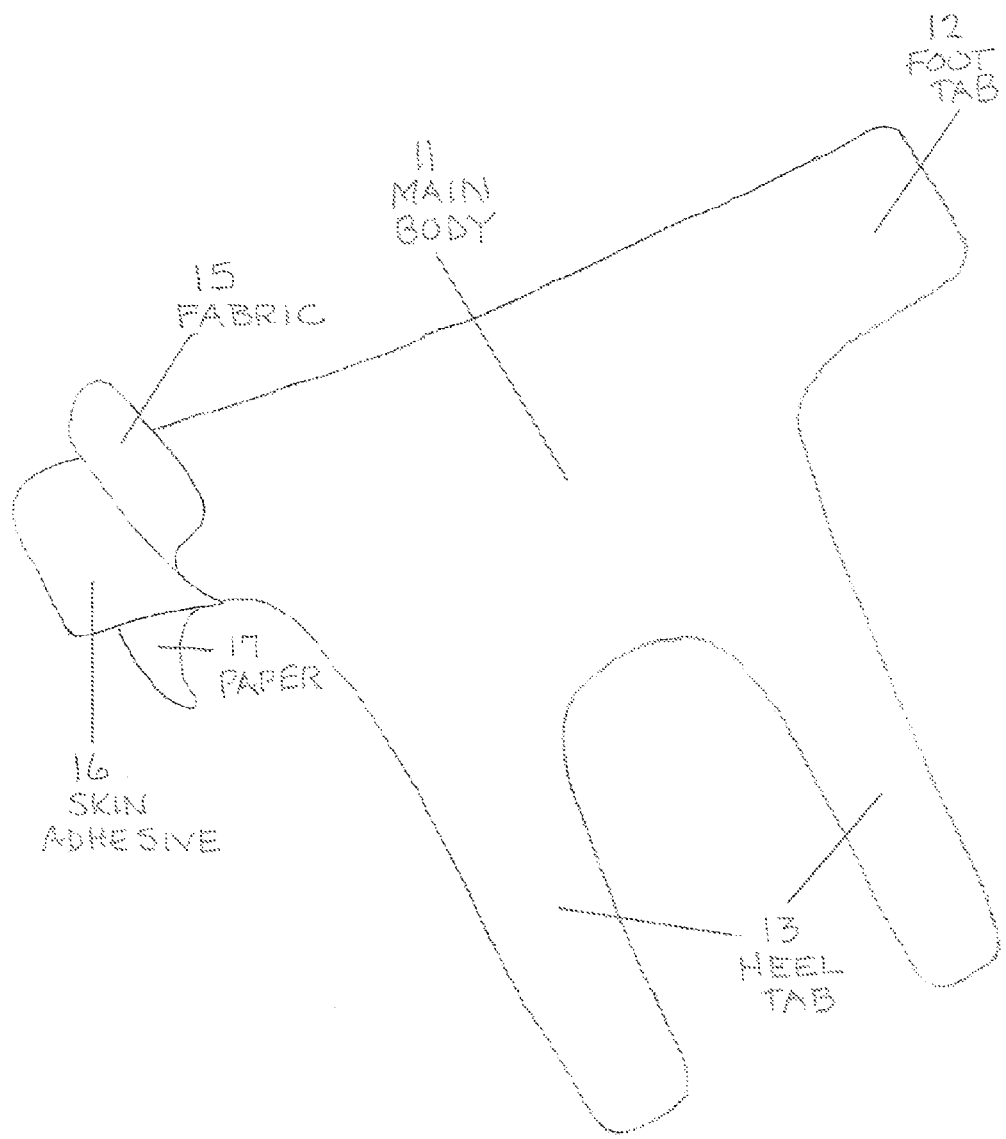
FIG. 1 Depicts a perspective view of the exterior, fabric side, of the foot support strap before it it applied to the foot.
Figure 2:
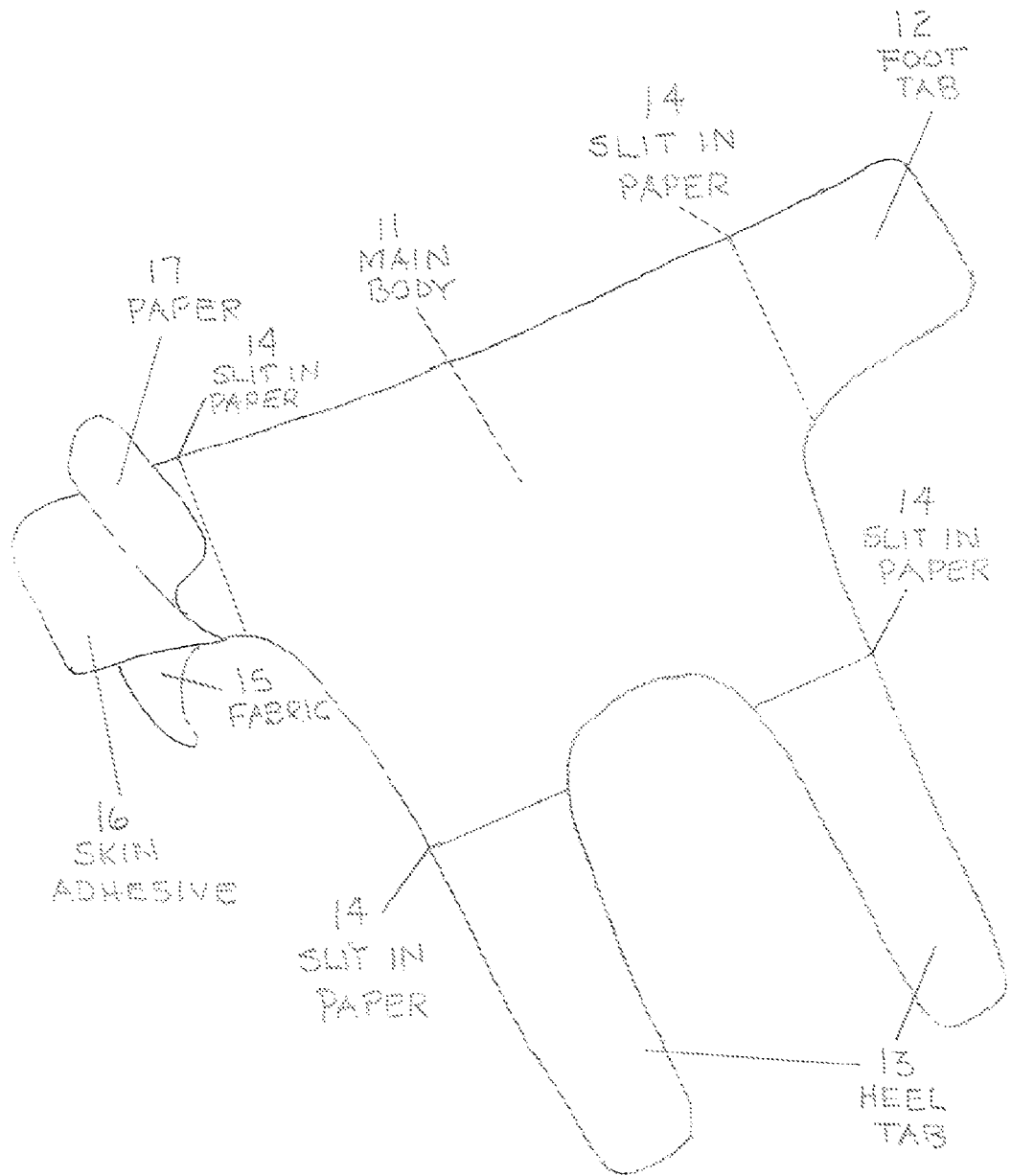
FIG. 2 Depicts a perspective view of the interior, paper covering side, of the foot support strap before it is applied to the foot.
Figure 3:
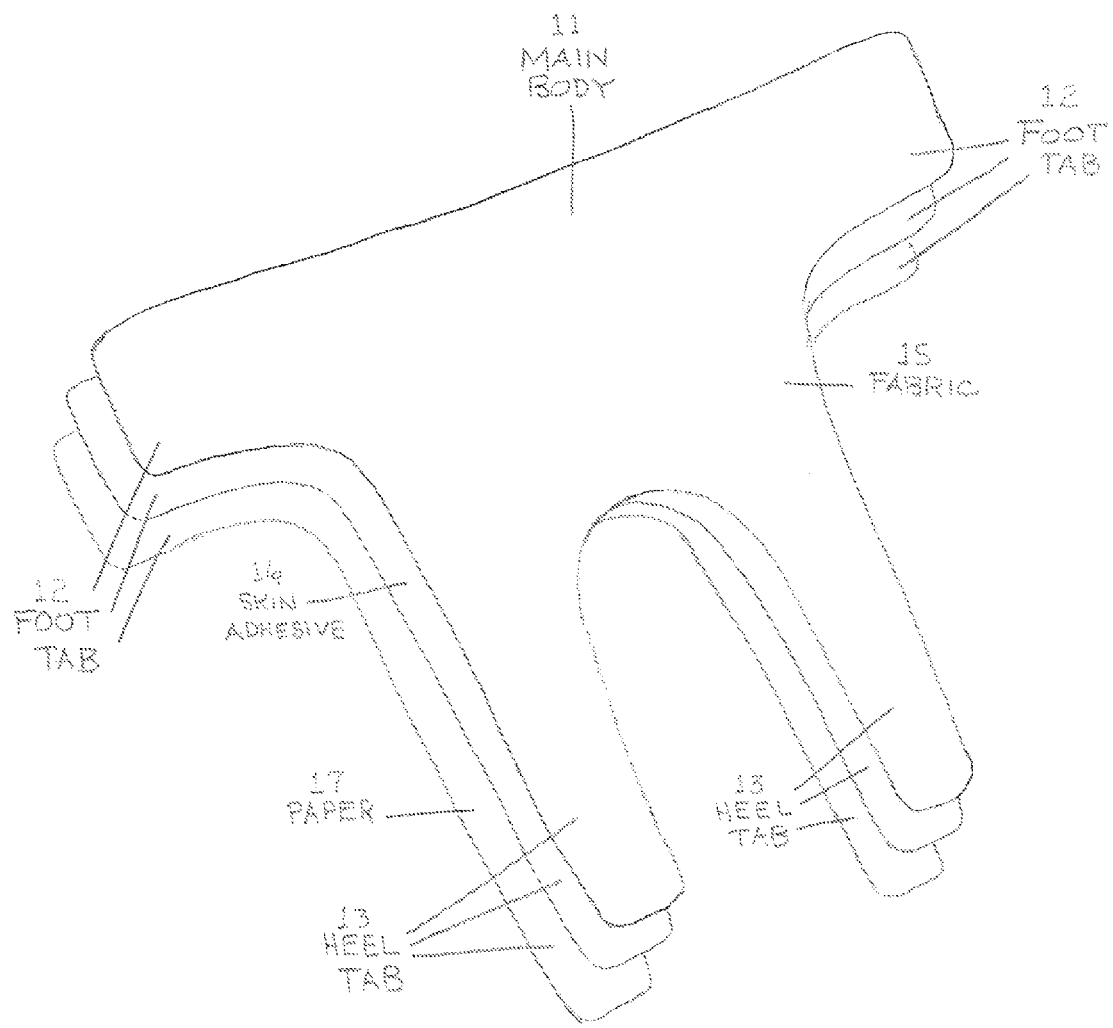
FIG. 3 Depicts a perspective view of the three layers of the foot support strap.

The illustrations in FIG. 1, FIG. 2 and FIG. 3 show that the foot support strap has three layers comprising of a one-piece fabric layer, a one-piece skin adhesive layer and a 5-piece paper layer. All three layers cover the entire shape of the foot support strap. The three layers together are approximately 1/64 of an inch in thickness.

The illustrations in FIG. 1, FIG. 2 and FIG. 3 also show the named parts of the foot support strap.

FIG. 1 depicts a perspective view of the exterior, fabric 15, of the foot support strap, before it is applied to the foot.

FIG. 1 depicts a perspective view of fabric 15, the exterior layer, comprising of a single piece of non-stretch or stretch resistant fabric of cotton or other textile content. Attached to the underside of fabric 15 is skin adhesive 16. Paper 17 is a removable paper coating that protects skin adhesive 16 until it is applied to the foot. Skin adhesive 16 is double sided, therefore it adheres to fabric 15 on one side and paper 17 on the other side.

FIG. 2 depicts a perspective view of the interior layer, paper 17, of an foot support strap.

FIG. 2 shows paper 17, the interior layer, comprising of paper that protects the skin adhesive 16 layer until the foot support strap is ready to be applied to the foot. Paper 17 includes four slits that separate paper 17 into five sections. The patient can remove paper 17, one section at a time, for ease of application since skin adhesive 16 is very sticky. All five sections of paper 17 will be completely removed during the application of the foot support strap.

FIG. 3 depicts a perspective view of the three layers of the foot support strap. All three layers are the same size and shape Skin adhesive 16 adheres all three layers together into one piece.

Figure 4:
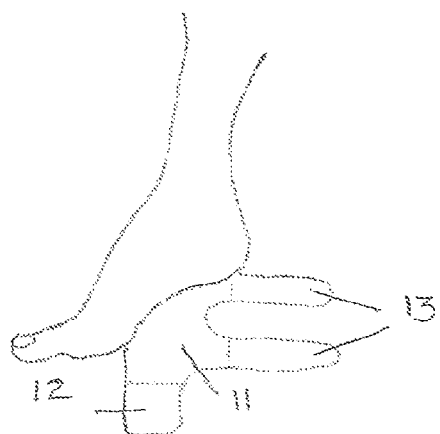
FIGS. 4 through 7 shows how to apply the foot support strap to the foot.

FIG. 4 shows the first step in applying the foot support strap. As shown in FIG. 4, after removing the protective paper from main body 11, user lifts only the heel of the foot off the floor. User centers the foot support strap with the foot and slides it under the foot until it stops at the pad of the foot.

Figure 5:
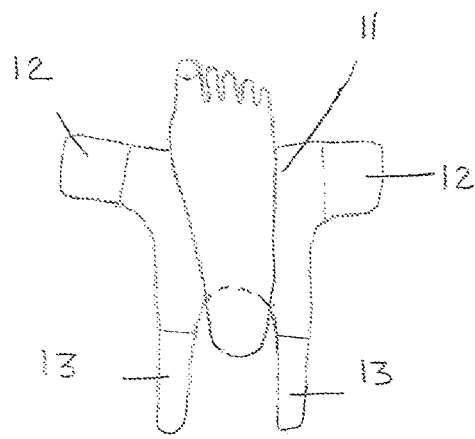

In FIG. 5, with the foot centered over the foot support strap, the user sets the heel down in the open space in between heel tabs 13.

Figure 6:
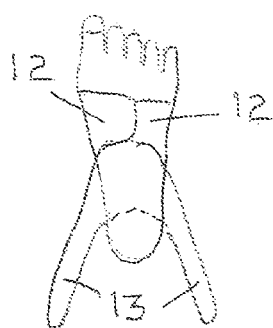

In FIG. 6, the patient removes the protective paper from foot tabs 12 and applies foot tabs 12, straight across, to the top of the foot.

Figure 7:
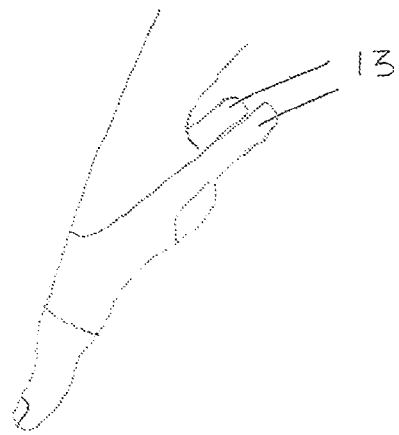

In FIG. 7, the patient removes the protective paper from heel tabs 13. Then lifts the foot off the floor. While bending the foot down and forward, or pointing the toe, the user pulls back firmly on both heel tabs 13. Then, one at a time, secures heel tabs 13 around the back of the heel in a position no higher than where a normal shoe would hit against the heel.

Figure 8:
FIG. 8 Depicts a perspective view of the foot support strap after it is applied to the foot.

FIG. 8 depicts a perspective view of the foot support strap after is has been applied to the foot.

User wears the disposable foot support strap for approximately 3 to 5 days, or until it starts to lose its effectiveness. At that time, the foot support strap is removed and discarded. Another disposable foot support strap may be applied immediately. The foot support strap can be worn continuously until the foot ailment has healed or can be worn as a preventative measure during sports activities, long hours on the feet and many other times when feet are in pain.

The foot support strap custom fits comfortably to each foot. It is very easy to use, economical, quick to apply, can be used with any type of socks, shoes, sandals or flip-flops with no disruption to user's daily routine. It can also be worn without any footwear at all.

Although the foot support strap has been described in conjunction with specific illustrations and embodiments, it will be understood by those skilled in the art that various changes may be made and equivalents may be substituted without departing from the scope of the foot support strap. Therefore, it is intended that the foot support strap not be limited to the particular embodiment disclosed, but that the invention will include all embodiments falling within the broad scope of the appended claims.

The invention claimed is:

1. A one-piece adhesive, fabric strap for treating and preventing plantar fasciitis and many other foot ailments by conforming to the shape of the foot and minimizing the tensile forces to the longitudinal and transverse axes of the foot comprising:
    a main body for placement beneath the ball of the foot and beneath the arch of the foot;
    a foot tab on each side, and attached to, the main body that wraps around the sides and top of the foot, thereby, forming a holding strap around the circumference of the foot;
    a heel tab on each side, and attached to the main body that runs along both sides of the foot and wraps around the back of the heel, thereby forming an opening on the bottom of the heel,
    said heel tabs having an opening located between them, said opening extending parallel along a substantial length of said heel tabs, an adhesive covering a substantial portion of said main body, said foot tabs and said heel tabs
    wherein, the main body, the foot tabs and the heel tabs form said one-piece adhesive fabric.

2. The adhesive fabric strap, according to claim 1, wherein the fabric consists of non-stretch fibers that run longitudinally in the direction parallel to the length of the foot when in use.

3. A method for treating and preventing plantar fasciitis and many other foot ailments according to claim 1, said method comprising: wherein to hold the heel and the ball of the foot together longitudinally with comfortable, non-stretch fabric, securing said fabric with an adhesive with great enough strength so to resist slippage due to shear stress and bear the weight of the user.

4. A method for treating and preventing plantar fasciitis and other foot ailments, according to claim 1, wherein the foot is not limited in any activity or footwear.

* * * * *